US012629095B2

(12) United States Patent
Lock et al.

(10) Patent No.: US 12,629,095 B2
(45) Date of Patent: May 19, 2026

(54) ANNULAR WEARABLE ELECTRONIC DEVICE

(71) Applicant: COAPT LLC, Chicago, IL (US)

(72) Inventors: Blair Andrew Lock, Wilmette, IL (US); Xavier Nigel Oberhelman, Chicago, IL (US); Katherine Amy Cai, Evanston, IL (US)

(73) Assignee: COAPT LLC, Chicago, IL (US)

( * ) Notice: Subject to any disclaimer, the term of this patent is extended or adjusted under 35 U.S.C. 154(b) by 556 days.

(21) Appl. No.: 18/124,964

(22) Filed: Mar. 22, 2023

(65) Prior Publication Data

US 2024/0315643 A1 Sep. 26, 2024

(51) Int. Cl.
| | |
|---|---|
| *G06F 1/16* | (2006.01) |
| *A61B 5/00* | (2006.01) |
| *H05K 5/00* | (2025.01) |
| *H05K 7/00* | (2006.01) |
| *G01D 11/30* | (2006.01) |

(52) U.S. Cl.
CPC .......... *A61B 5/6802* (2013.01); *A61B 5/7264* (2013.01); *A61B 2562/0219* (2013.01); *G01D 11/30* (2013.01)

(58) Field of Classification Search
CPC ..... G06F 1/163; A61B 5/6802; A61B 5/7264; A61B 2562/0219
See application file for complete search history.

(56) References Cited

U.S. PATENT DOCUMENTS

| | | | | |
|---|---|---|---|---|
| 4,817,064 A | * | 3/1989 | Milles ................ | G04B 37/1486 |
| | | | | 968/374 |
| 5,214,623 A | * | 5/1993 | Seager ................... | H04B 1/385 |
| | | | | 379/430 |
| 5,228,012 A | * | 7/1993 | Seager ................. | A44C 5/0007 |
| | | | | 368/282 |
| 5,251,189 A | * | 10/1993 | Thorp ................. | A44C 5/0007 |
| | | | | 379/430 |
| 5,260,915 A | * | 11/1993 | Houlihan ............... | G04B 47/00 |
| | | | | 224/931 |
| D460,430 S | * | 7/2002 | Wada ............................. | D10/31 |
| D466,488 S | * | 12/2002 | Wada ............................. | D10/31 |
| 8,098,141 B2 | * | 1/2012 | Vanska ............... | G06F 3/03547 |
| | | | | 340/407.1 |
| 8,725,842 B1 | * | 5/2014 | Al-Nasser .............. | G04G 21/08 |
| | | | | 709/219 |
| 9,285,830 B2 | * | 3/2016 | Alcazar ................... | G06F 1/163 |
| 9,299,248 B2 | | 3/2016 | Lake et al. | |

(Continued)

FOREIGN PATENT DOCUMENTS

EP 2959394 B1 5/2021

OTHER PUBLICATIONS

European Patent Application No. 24162654.8, Extended European Search Report, dated May 27, 2024.

*Primary Examiner* — Anthony M Haughton
(74) *Attorney, Agent, or Firm* — MARSHALL, GERSTEIN & BORUN LLP

(57) ABSTRACT

An annuler wearable electronic device includes a plurality of interconnected sensor pods. Each sensor pod includes one or more biosensors configured to collect biometric signal data of a user and each sensor pod is coupled to at least one adjacent sensor pod via a rigid, non-elastic coupling arm such that a circumference of the wearable electronic device is variable.

22 Claims, 13 Drawing Sheets

(56) References Cited

U.S. PATENT DOCUMENTS

| | | | |
|---|---|---|---|
| 9,372,535 B2 | 6/2016 | Bailey et al. | |
| 9,408,316 B2 | 8/2016 | Bailey et al. | |
| 9,483,123 B2 | 11/2016 | Aleem et al. | |
| 9,600,030 B2 | 3/2017 | Bailey et al. | |
| 9,703,322 B2 * | 7/2017 | Lin | A44C 5/0053 |
| 9,874,901 B2 * | 1/2018 | Seok | G06F 1/1637 |
| 9,880,632 B2 * | 1/2018 | Ataee | G06F 18/2415 |
| 10,016,161 B2 * | 7/2018 | Townsend | A61B 5/742 |
| 10,152,082 B2 * | 12/2018 | Bailey | G06F 1/1656 |
| 10,289,158 B2 * | 5/2019 | Hiroki | G06F 1/1652 |
| 10,338,638 B2 * | 7/2019 | Park | G06F 1/163 |
| 10,607,507 B2 * | 3/2020 | Connor | A61B 5/4866 |
| 11,009,951 B2 | 5/2021 | Bailey et al. | |
| 11,775,066 B2 | 10/2023 | Lock et al. | |
| 11,797,087 B2 * | 10/2023 | Barachant | G06N 3/0442 |
| 11,868,531 B1 * | 1/2024 | Tasci | G06N 20/00 |
| 2005/0120746 A1 | 6/2005 | Winston et al. | |
| 2012/0203076 A1 * | 8/2012 | Fatta | A61B 5/681 |
| | | | 600/300 |
| 2014/0070957 A1 * | 3/2014 | Longinotti-Buitoni | |
| | | | G06F 1/163 |
| | | | 340/870.01 |
| 2014/0240103 A1 | 8/2014 | Lake et al. | |
| 2014/0334083 A1 * | 11/2014 | Bailey | G06F 1/1692 |
| | | | 361/679.03 |
| 2015/0051470 A1 * | 2/2015 | Bailey | G06F 3/015 |
| | | | 600/300 |
| 2015/0234426 A1 * | 8/2015 | Bailey | A61B 5/6831 |
| | | | 427/96.1 |
| 2015/0370326 A1 * | 12/2015 | Chapeskie | G06F 1/163 |
| | | | 345/156 |
| 2018/0042513 A1 * | 2/2018 | Connor | A61B 5/369 |
| 2018/0150033 A1 | 5/2018 | Lake et al. | |
| 2025/0076983 A1 * | 3/2025 | Chang | G06F 3/017 |

* cited by examiner 105,105a

ANNULAR WEARABLE ELECTRONIC DEVICE

STATEMENT REGARDING FEDERALLY SPONSORED RESEARCH OR DEVELOPMENT

This invention was made with government support under Intuitively Controlled Virtual Reality to Treat Phantom Limb Pain, No. W81XWH2010873, awarded by the Defense Health Program, Congressionally Directed Medical Research Programs, USA MED RESEARCH ACQ ACTIV-ITY. The government has certain rights in the invention.

FIELD OF THE INVENTION

This disclosure relates generally to wearable electronic devices and, more particularly, to annular wearable electronic devices to be worn on a limb of a user.

BACKGROUND

Wearable electronic devices can be worn by users, for example on an arm, to detect movement of the limb or muscle activation in the limb. However, existing wearable devices can exhibit problems associated with data fidelity and/or lack of fit due to the lack of adaptability of the structural configuration of a wearable electronic device.

Accordingly, there is a need for annular wearable electronic devices to be worn on a limb of a user, as described herein.

SUMMARY

In accordance with one exemplary aspect of the present invention, an annular wearable electronic device comprises a plurality of interconnected sensor pods. Each of the plurality of sensor pods includes one or more biosensors configured to collect biometric signal data of a user and each sensor pod of the plurality of sensor pods is coupled to at least one adjacent sensor pod via a rigid, non-elastic coupling arm such that a circumference of the wearable electronic device is variable. The biometric signal data can then be used for various purposes, such as electronic determination of gestures, display control, virtual reality control, etc.

In further accordance with any one or more of the foregoing exemplary aspects of the present invention, an annular wearable electronic device may further include, in any combination, any one or more of the following preferred forms.

In one preferred form, each of the sensor pods comprises a longitudinal axis; and the longitudinal axes of adjacent sensor pods are generally parallel with a longitudinal axis of a limb of a user wearing the wearable electronic device with the wearable electronic device in a retracted position and generally non-parallel with the longitudinal axis of the limb of the user with the wearable electronic device in an expanded position.

In another preferred form, each coupling arm is rotatably coupled to opposite ends of adjacent sensor pods.

In another preferred form, each sensor pod comprises a position sensor to measure a rotational position of the coupling arm relative to the sensor pod.

In another preferred form, each sensor pod includes a spring configured to act on a respective coupling arm to bias adjacent sensor pods toward a retracted position.

In another preferred form, the one or more biosensors comprise: (a) one or more electromyography (EMG) electrodes; (b) one or more electrocardiogram electrodes; (c) one or more photodiodes; (d) one or more ultrasound transducers; (e) one or more accelerometers; (f) one or more gyroscopes; (g) one or more infrared sensors; and/or (h) one or more ultrasound sensors.

In another preferred form, the annular wearable electronic device comprises a processor communicatively coupled to the one or more biosensors, a transceiver communicatively coupled to the processor, and a memory. The memory storing computing instructions, which when executed by the processor, causes the processor to implement at least one of: (a) collect the biometric signal data of the user and transmit the biometric signal data to a computing device, wherein the computing device is configured to: (1) generate an analysis of the biometric signal data of the user; and/or (2) display the biometric signal data and/or the analysis thereof on a display screen of the computing device; (b) receive an input from a computing device to configure or alter an operation or setting of the wearable electronic device; and/or (c) provide an indication of an operation or status of the wearable electronic device via at least one light emitting diode of a sensor pod of the plurality of sensor pods.

In accordance with another exemplary aspect of the present invention, an annular wearable electronic device comprises a plurality of interconnected sensor pods. Each of the plurality of sensor pods includes one or more biosensors configured to collect biometric signal data of a user and each sensor pod of the plurality of sensor pods is coupled to at least one adjacent sensor pod via a rigid, non-elastic coupling arm. Each coupling arm is rotatable relative to each corresponding sensor pod such that a circumference of the wearable electronic device is variable.

In further accordance with any one or more of the foregoing exemplary aspects of the present invention, an annular wearable electronic device may further include, in any combination, any one or more of the following preferred forms.

In one preferred form, each of the sensor pods comprises a longitudinal axis; and the longitudinal axes of adjacent sensor pods are generally parallel with a longitudinal axis of a limb of a user wearing the wearable electronic device with the wearable electronic device in a retracted position and generally non-parallel with the longitudinal axis of the limb of the user with the wearable electronic device in an expanded position.

In another preferred form, each coupling arm is rotatably coupled to opposite ends of adjacent sensor pods.

In another preferred form, each sensor pod comprises a position sensor to measure a rotational position of the coupling arm relative to the sensor pod.

In another preferred form, each sensor pod includes a spring configured to act on a respective coupling arm to bias adjacent sensor pods toward a retracted position.

In another preferred form, the one or more biosensors comprise: (a) one or more electromyography (EMG) electrodes; (b) one or more electrocardiogram electrodes; (c) one or more photodiodes; (d) one or more ultrasound transducers; (e) one or more accelerometers; (f) one or more gyroscopes; (g) one or more infrared sensors; and/or (h) one or more ultrasound sensors.

In another preferred form, the annular wearable electronic device comprises a processor communicatively coupled to the one or more biosensors, a transceiver communicatively coupled to the processor, and a memory. The memory storing computing instructions, which when executed by the processor, causes the processor to implement at least one of: (a) collect the biometric signal data of the user and transmit the biometric signal data to a computing device, wherein the computing device is configured to: (1) generate an analysis of the biometric signal data of the user; and/or (2) display the biometric signal data and/or the analysis thereof on a display screen of the computing device; (b) receive an input from a computing device to configure or alter an operation or setting of the wearable electronic device; and/or (c) provide an indication of an operation or status of the wearable electronic device via at least one light emitting diode of a sensor pod of the plurality of sensor pods.

In accordance with another exemplary aspect of the present invention, an annular wearable electronic device comprises a plurality of interconnected sensor pods. Each sensor pod of the plurality of sensor pods including one or more biosensors configured to collect biometric signal data of a user and a plurality of light emitting diodes. The plurality of light emitting diodes of each sensor pod are configured to illuminate in a predetermined pattern to indicate a strength of a signal detected by the one or more biosensors of the sensor pod.

In further accordance with any one or more of the foregoing exemplary aspects of the present invention, an annular wearable electronic device may further include, in any combination, any one or more of the following preferred forms.

In one preferred form, the predetermined pattern comprises one or more of: a predefined set of one or more colors; a predefined set of one or more illumination intensities; and/or a predefined sequence of activating one or more of the plurality of light emitting diodes.

In another preferred form, each of the sensor pods comprises a longitudinal axis and the longitudinal axes of adjacent sensor pods are generally parallel with a longitudinal axis of a limb of a user wearing the wearable electronic device with the wearable electronic device in a retracted position and generally non-parallel with the longitudinal axis of the limb of the user with the wearable electronic device in an expanded position.

In another preferred form, each coupling arm is rotatably coupled to opposite ends of adjacent sensor pods.

In another preferred form, each sensor pod comprises a position sensor to measure a rotational position of the coupling arm relative to the sensor pod.

In another preferred form, each sensor pod includes a spring configured to act on a respective coupling arm to bias adjacent sensor pods toward a retracted position.

In another preferred form, the one or more biosensors comprise: (a) one or more electromyography (EMG) electrodes; (b) one or more electrocardiogram electrodes; (c) one or more photodiodes; (d) one or more ultrasound transducers; (e) one or more accelerometers; (f) one or more gyroscopes; (g) one or more infrared sensors; and/or (h) one or more ultrasound sensors.

In another preferred form, the annular wearable electronic device comprises a processor communicatively coupled to the one or more biosensors, a transceiver communicatively coupled to the processor, and a memory. The memory storing computing instructions, which when executed by the processor, causes the processor to implement at least one of: (a) collect the biometric signal data of the user and transmit the biometric signal data to a computing device, wherein the computing device is configured to: (1) generate an analysis of the biometric signal data of the user; and/or (2) display the biometric signal data and/or the analysis thereof on a display screen of the computing device; (b) receive an input from a computing device to configure or alter an operation or setting of the wearable electronic device; and/or (c) provide an indication of an operation or status of the wearable electronic device via at least one of the plurality of light emitting diode of at least one of the plurality of sensor pods.

In accordance with the above, and with the disclosure herein, the present disclosure includes improvements in computer functionality or in improvements to other technologies at least because the claims recite that, e.g., an annular wearable electronic device comprising a plurality of interconnected sensor pods, where each of the plurality of sensor pods include one or more biosensors configured to collect biometric signal data of a user. That is, the present disclosure describes improvements in the functioning of the computer itself or "any other technology or technical field" because the configuration of the annular wearable electronic device allows for an improvement in the data fidelity and/or data collection or sensing because the annular wearable electronic device is configured to be worn on a limb of a user and be expandable to fit most upper and lower limbs, such as arms or legs, of a given user. This improves over the prior art at least because the device provides an increased adaptable fit, leading to improved electrode-to-user contact, and thus resulting in improved data biometric signal data collection, and data fidelity, from a user.

Further, the present disclosure includes applying certain of the claim elements with, or by use of, a particular machine, e.g., an annular wearable electronic device.

Still further, the present disclosure includes effecting a transformation or reduction of a particular article to a different state or thing, e.g., transformation of biometric signal data of a user, as collected or sensed by the annular wearable electronic device, into data for use by computing instructions to, including, by way of non-limiting example, reduce/control phantom limb pain, to control a prosthetic device, to manipulate a virtual avatar in a virtual reality system, or otherwise, for example, as described herein.

Still further, the present disclosure includes specific features other than what is well-understood, routine, conventional activity in the field, and/or otherwise adds unconventional steps that confine the disclosure to a particular useful application, e.g., an annular wearable electronic device comprising a plurality of interconnected sensor pods, where each of the plurality of sensor pods include one or more biosensors configured to collect biometric signal data of a user.

Advantages will become more apparent to those of ordinary skill in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The figures described below depict various aspects of the systems and devices disclosed therein. It should be understood that each figure depicts an embodiment of a particular aspect of the disclosed systems and devices, and that each of the figures is intended to accord with a possible embodiment thereof. Further, wherever possible, the following description refers to the reference numerals included in the following figures, in which features depicted in multiple figures are designated with consistent reference numerals.

There are shown in the drawings arrangements which are presently discussed, it being understood, however, that the present embodiments are not limited to the precise arrangements and instrumentalities shown, wherein.

Figure 1:
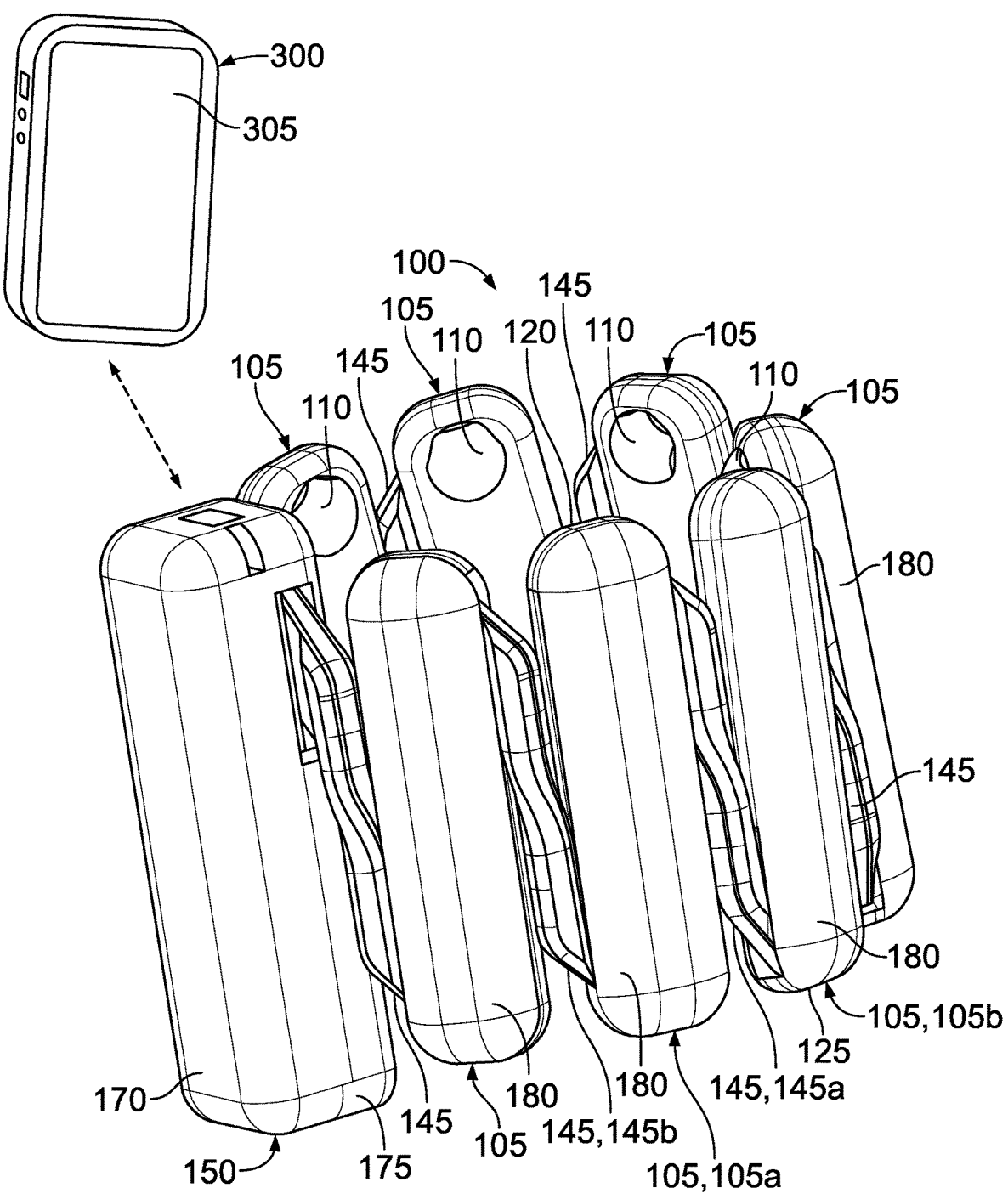
FIG. 1 is a perspective view of an example annular wearable electronic device and a computing device in communication with the wearable electronic device.

The figures depict preferred embodiments for purposes of illustration only. Alternative embodiments of the systems and methods illustrated herein may be employed without departing from the principles of the invention described herein.

DETAILED DESCRIPTION

The example annular wearable electronic device shown and described herein includes multiple sensor pods that have embedded biosensors and a main pod that is in communication with the sensor pods and includes a processor, transceiver, and memory for receiving and processing signals from the sensor pods. Each of the sensor pods and the main pod are connected to adjacent pods with rigid, non-elastic coupling arms that are rotatable relative to the respective sensor pods, which allows the wearable electronic device to be worn on a limb of a user and be expandable to fit most upper and lower limbs, such as arms or legs, of a user. The wearable electronic device can be used to detect or predict gestures and gesture intentions (e.g., by amputees) and to transmit signals representative of these gestures and/or gesture intentions to a computing device, such as a smartphone, virtual reality (VR) headset, etc., which can use the signals received from the wearable electronic device for various purposes, such as to reduce/control phantom limb pain, to control a prosthetic device, manipulate a virtual avatar in a virtual reality system, etc., some examples of which are described in U.S. patent application Ser. No. 17/237,309, filed Apr. 22, 2021, and entitled "BIOMETRIC ENABLED VIRTUAL REALITY SYSTEMS AND METHODS FOR DETECTING USER INTENTIONS AND MANIPULATING VIRTUAL AVATAR CONTROL BASED ON USER INTENTIONS FOR PROVIDING KINEMATIC AWARENESS IN HOLOGRAPHIC SPACE, TWO-DIMENSIONAL (2D), OR THREE-DIMENSIONAL (3D) VIRTUAL SPACE", which is incorporated by reference herein in its entirety.

Referring to FIGS. 1-3C, an example annular wearable electronic device 100 is shown that includes a plurality of interconnected sensor pods 105 and a main pod 150 interconnected with two adjacent sensor pods 105 on opposite sides of main pod 150. Each sensor pod 105 is coupled to at least one adjacent sensor pod 105, or to main pod 150, via a rigid, non-elastic coupling arm 145 that is rotatable relative to the respective sensor pod 105 or main pod 150 such that a circumference of wearable electronic device 100 is variable. For example, wearable electronic device 100 can have a smaller circumference in a retracted position (FIGS. 2A-2C) and can be expanded to have a larger circumference in an expanded position (FIGS. 3A-3C) to fit a particular limb 200 of a user. In the example shown, wearable electronic device 100 includes eight sensor pods 105 and one main pod 150. However, wearable electronic device 100 could include any number of sensor pods 105 or main pods 150, depending on the size and particular application. Wearable electronic device 100 can communicate with a computing device 300, such as a smartphone, laptop, personal computer (PC), and/or, other computing device. In some embodiments, the wearable device 100 can communicate with multiple computing devices. Computing device 300 and wearable device 100 may be communicatively coupled, for example, through one or more wired or wireless standards, such as via the BLUETOOTH wireless technology standard, the WI-FI wireless technology standard, a cellular connection or other mobile device communication standard (e.g., such as 4G Long Term Evolution (LTE), 5G New Radio (NR), etc.), or the like.

Referring to FIGS. 4-8, each sensor pod 105 includes one or more biosensors 110 that include a portion that extends through a rear housing 185 of sensor pod 105. Biosensors 110 are configured to detect and collect biometric signal data and/or motion data of the user, which can be used to detect or predict gestures and/or gesture intentions of the user of wearable electronic device 100. For example, biosensors 110 could be electromyography (EMG) electrodes, electrocardiogram electrodes, photodiodes, ultrasound transducers, accelerometers, gyroscopes, infrared sensors, and/or ultrasound sensors. In the example shown, biosensors 110 are EMG electrodes that measure muscle response or electrical activity in the limb of the user.

Figure 4:
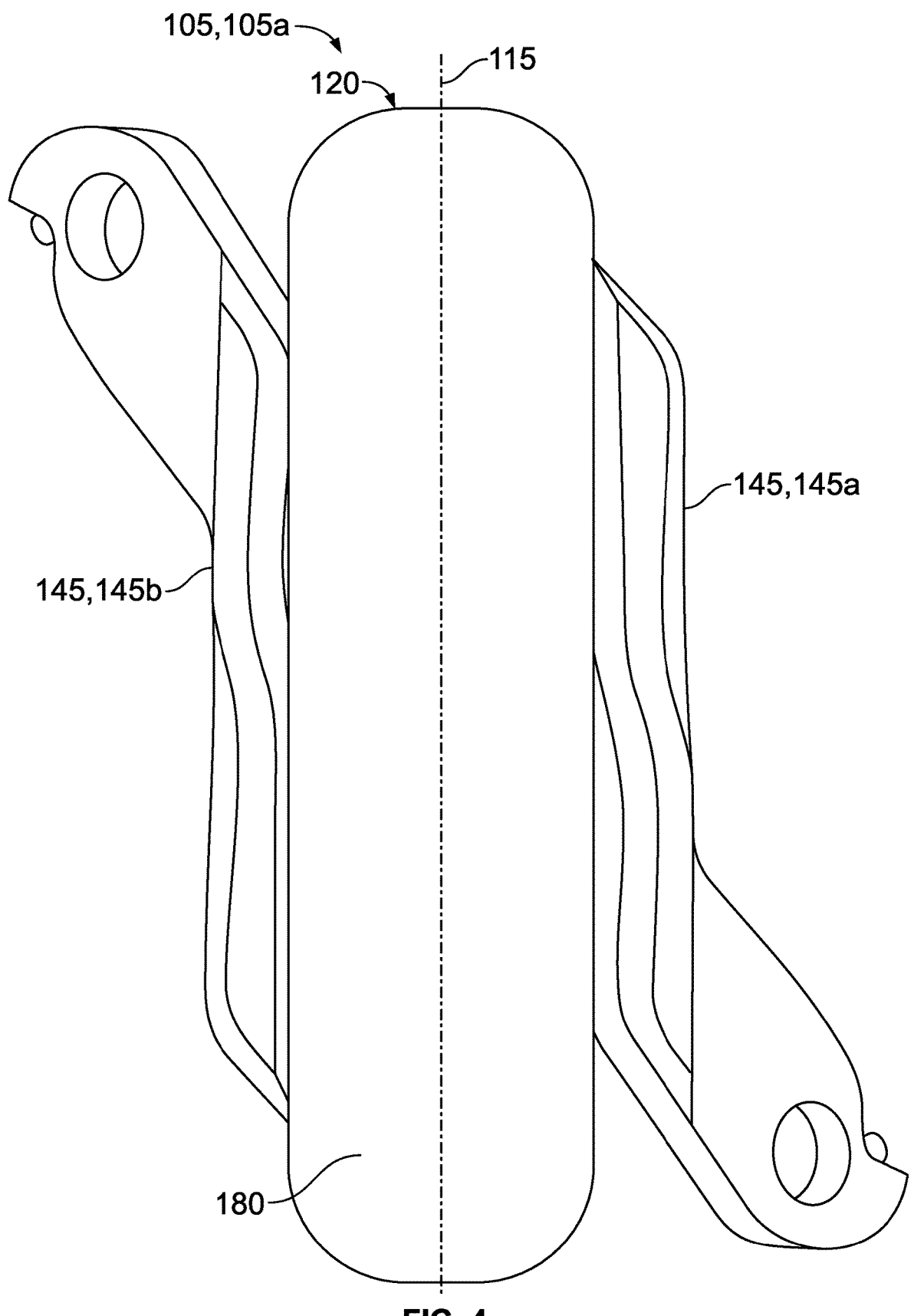
FIG. 4 is a front view of an example sensor pod of the wearable electronic device of FIG. 1 with two coupling arms.
Figure 6:
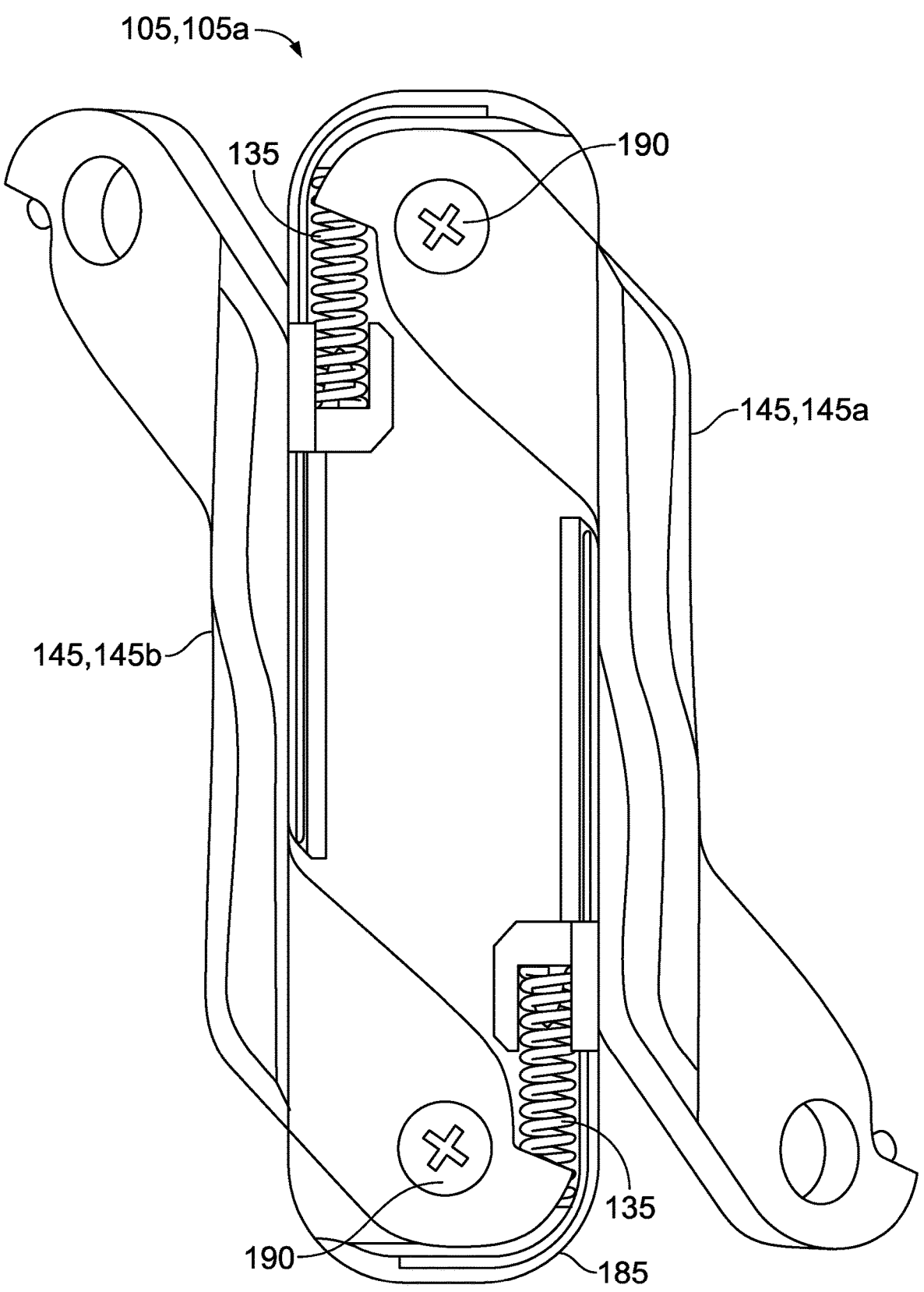
FIG. 6 is a front view of the sensor pod of FIG. 4 with the front housing and printed circuit board removed.
Figure 7:
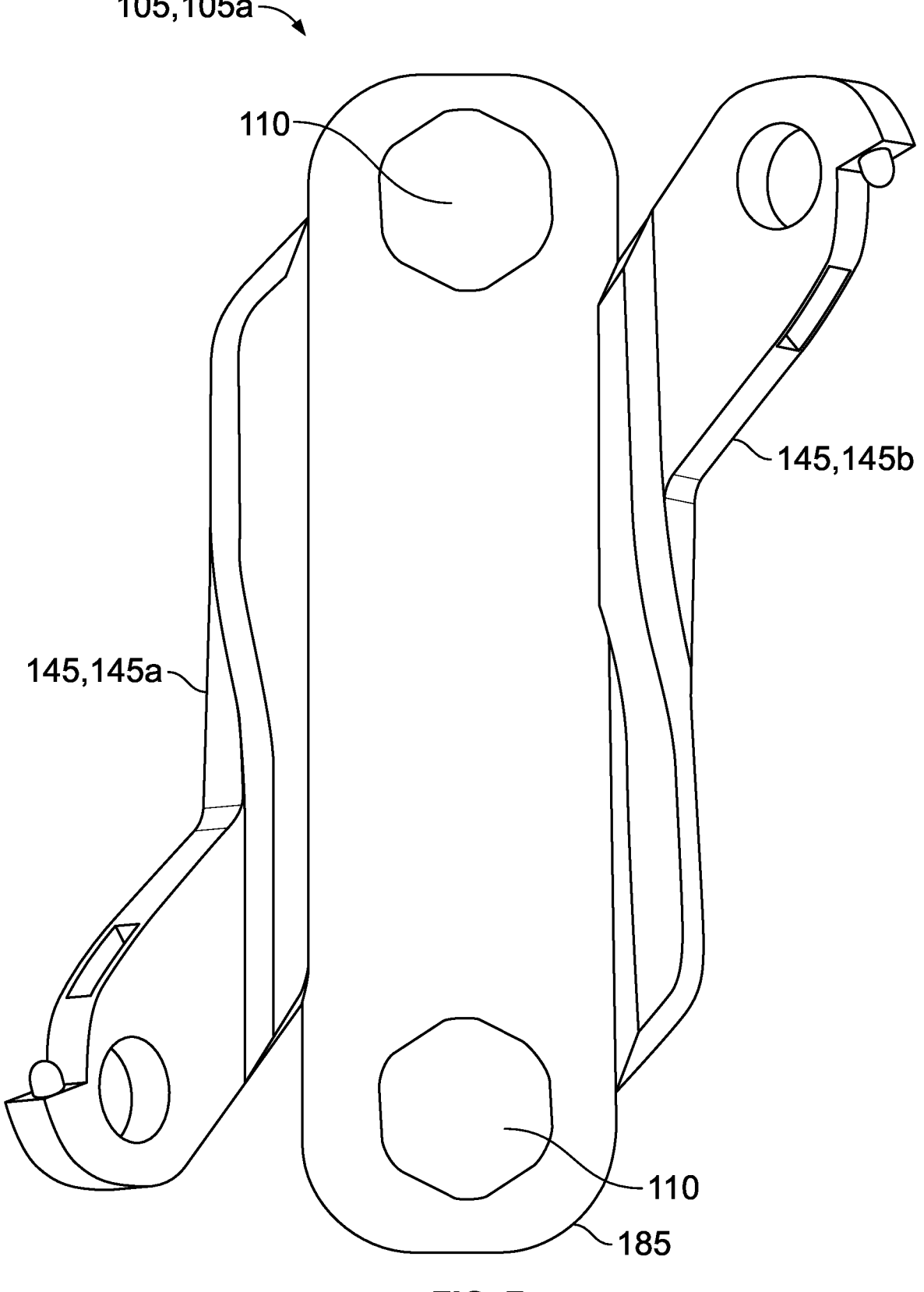
FIG. 7 is a rear view of the sensor pod of FIG. 4.
Figure 8:
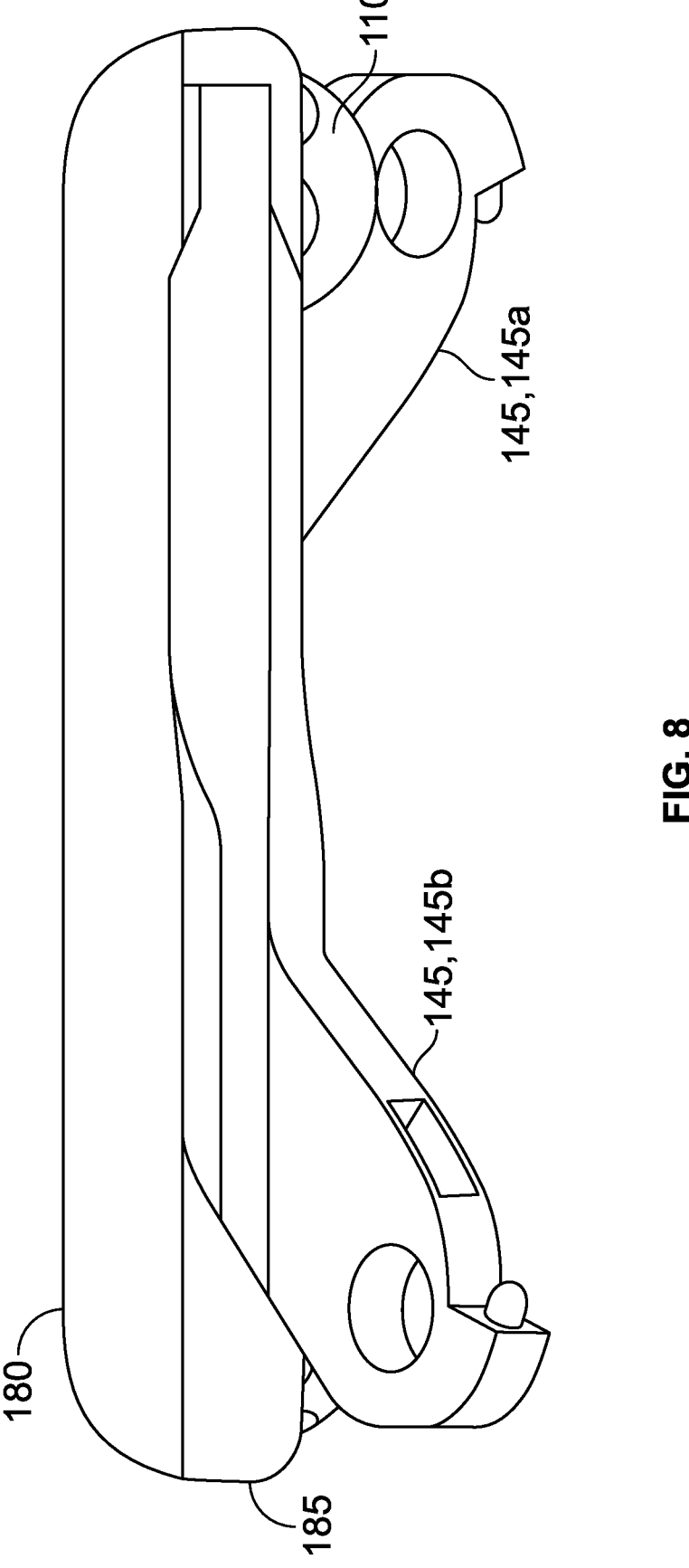
FIG. 8 is a side view of the sensor pod of FIG. 4.

In the example shown, each sensor pod 105 is rotatably coupled to two coupling arms (indicated as 145*a* and 145*b*), positioned on opposite lateral sides of sensor pod 105. Each coupling arm 145 is rotatably coupled to opposite ends of adjacent sensor pods 105. For example, as seen in FIGS. 1, 4, and 6, coupling arm 145*a* can be rotatably coupled to a first end 120 of a first sensor pod (indicated as 105*a*) at one end of coupling arm 145*a* and rotatably coupled to an opposite second end 125 of an adjacent second sensor pod (indicated as 105*b*) at an opposite end of coupling arm 145*a*. In the example shown, coupling arms 145 are rotatably coupled to sensor pods 105 via threaded members 190 that extend through holes in coupling arms 145 and are threaded into threaded apertures in rear housings 185 of sensor pods 105, but could be rotatably coupled in any appropriate manner desired. Each sensor pod 105 can also include a spring 135 (see, e.g., FIG. 6) that is configured to act on a respective coupling arm 145 that is rotatably coupled to sensor pod 105 to bias coupling arm 145 in a direction to bias adjacent sensor pods 105 toward the retracted position (see FIGS. 2A-C).

Each sensor pod 105 can also include a position sensor 130 that is configured to measure the rotational position of respective coupling arm(s) 145 relative to sensor pod 105. The rotational position measured by position sensor 130 can be used, for example, to determine the extent of expansion, and therefore the circumference, of wearable electronic device 100. The extent of expansion of wearable electronic device 100 could be used, for example, to determine or estimate which limb of the user wearable electronic device 100 is being worn on (e.g., upper arm, forearm, calf, thigh, etc.), which could be used to assist in the analysis of the signals received by computing device 300 from wearable electronic device 100.

Figures 2A, 2B:
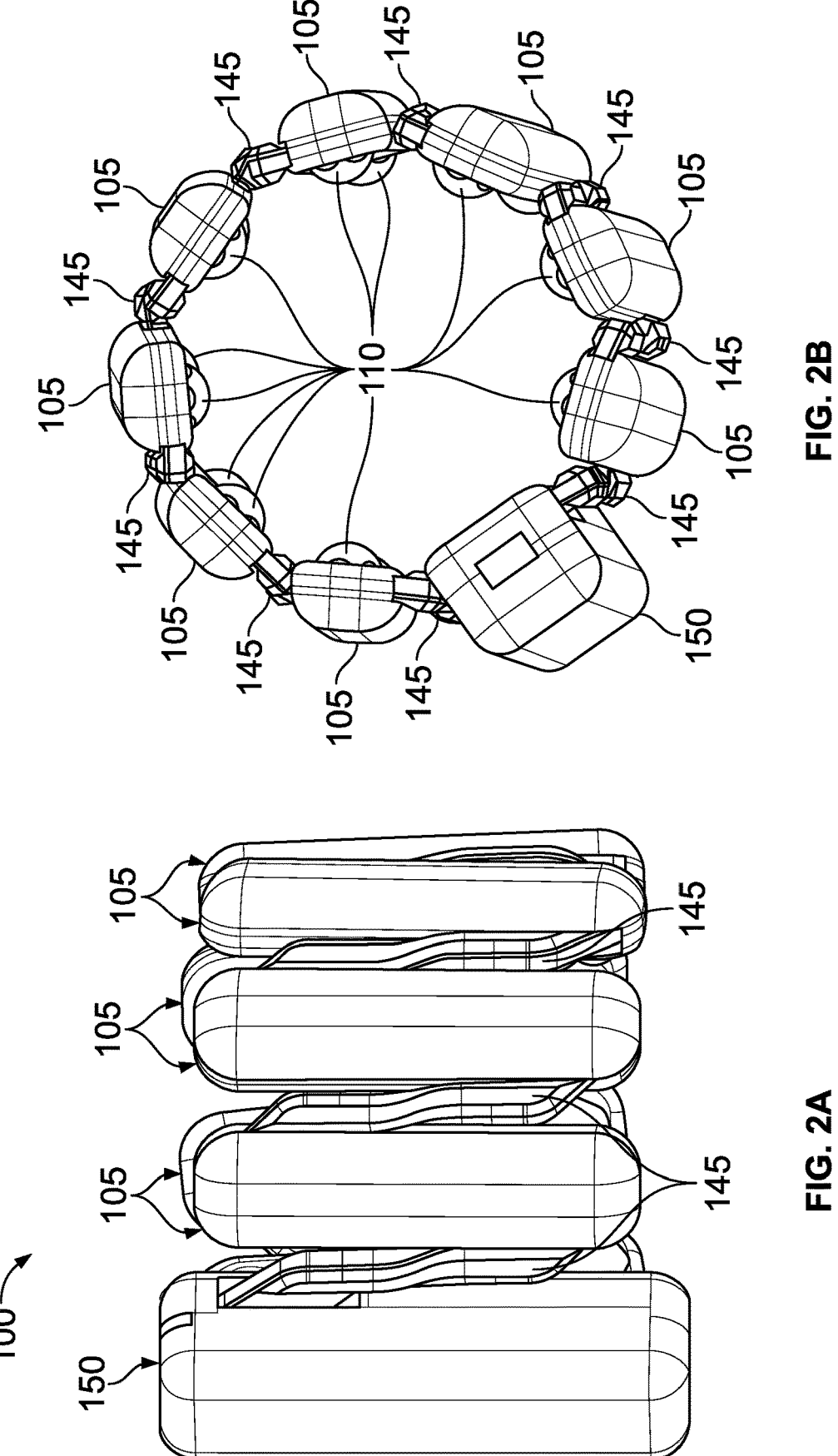
FIG. 2A is a side view of the wearable electronic device of FIG. 1 in the retracted position.
FIG. 2B is a top view of the wearable electronic device of FIG. 2A.
Figure 2C:
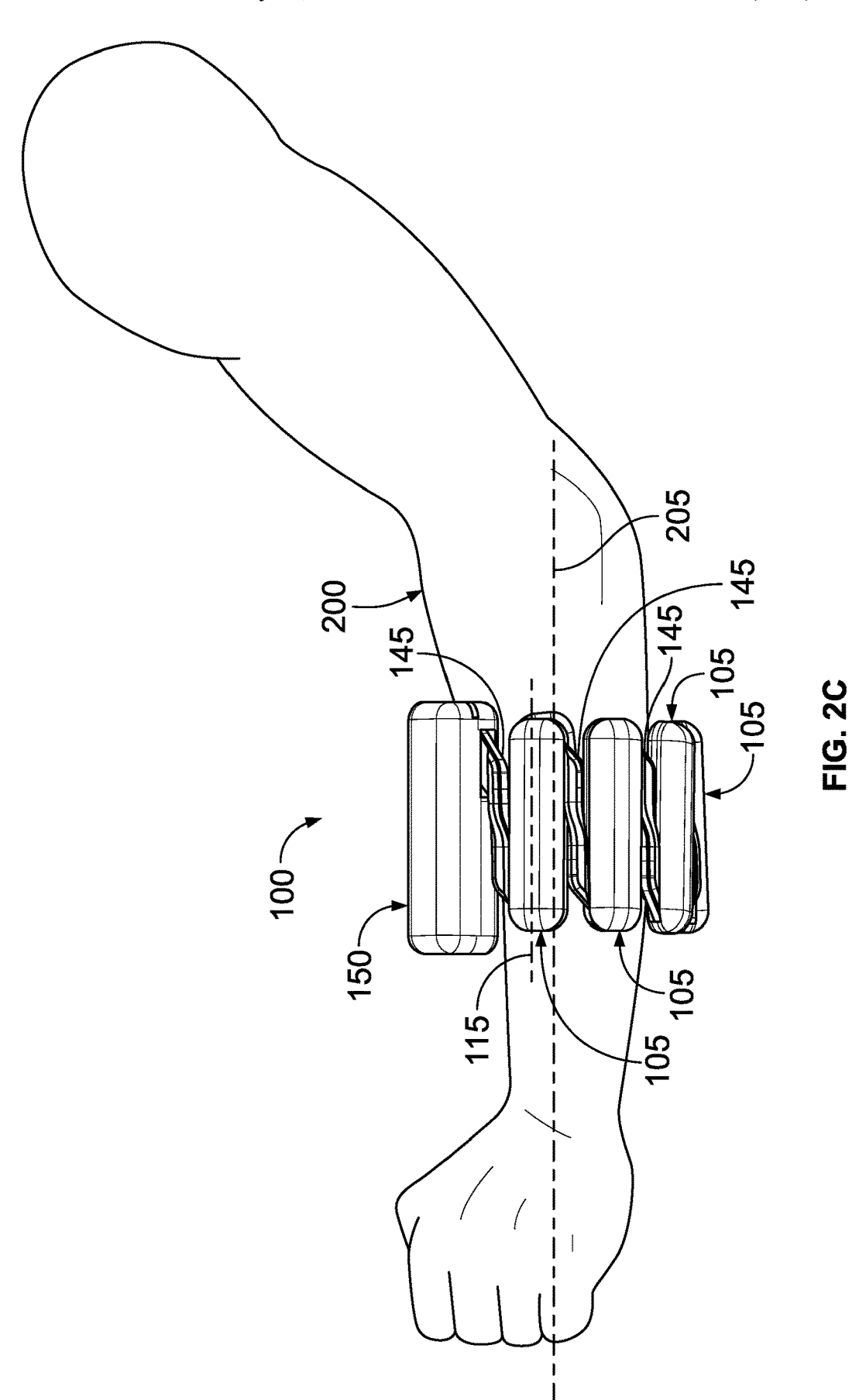
FIG. 2C is a side view of the wearable electronic device of FIG. 2A on a limb (arm) of a user.
Figure 3A:
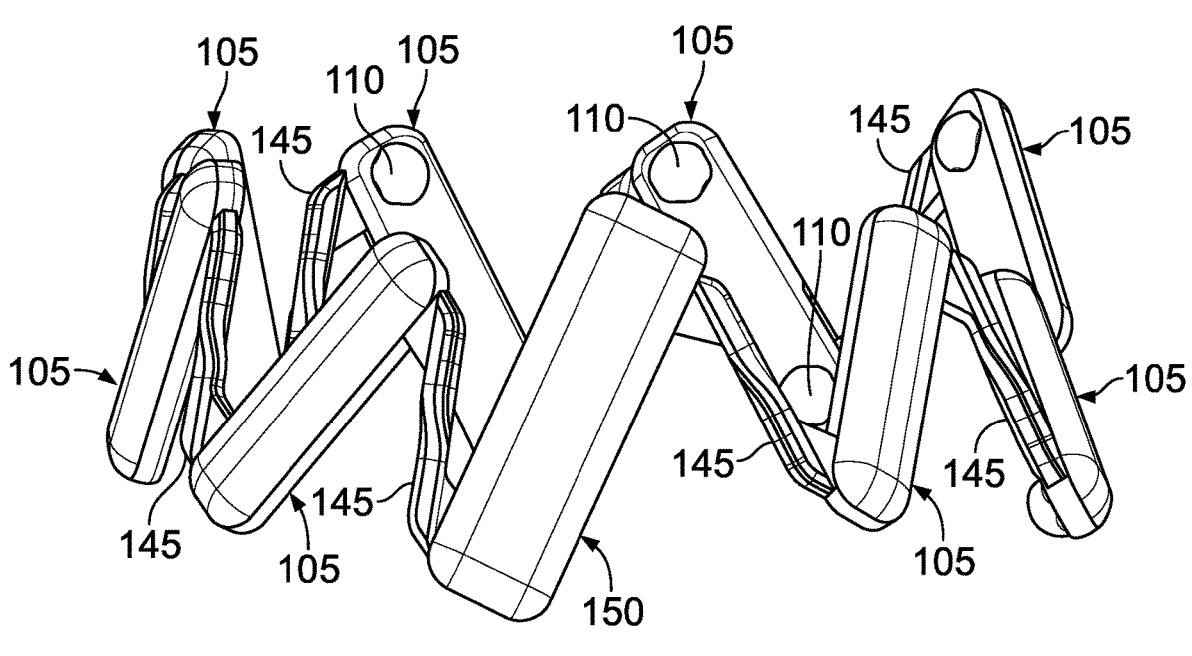
FIG. 3A is a side view of the wearable electronic device of FIG. 1 in an expanded position.
Figure 3B:
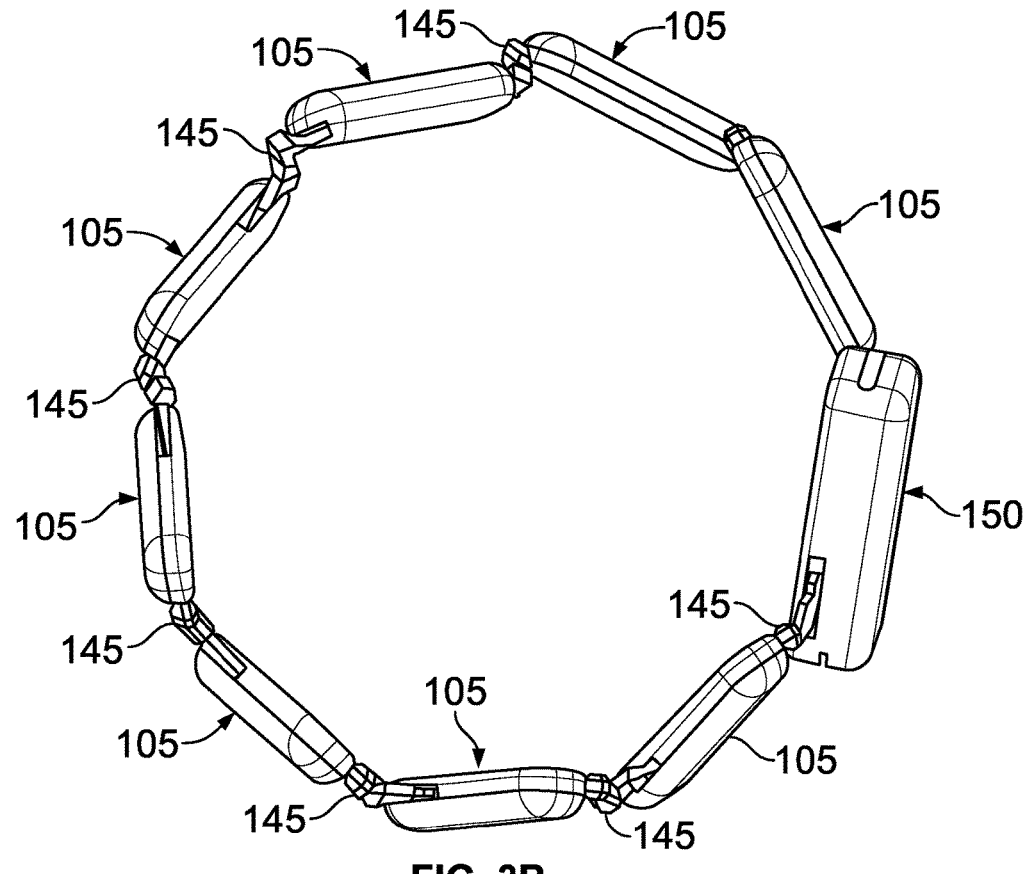
FIG. 3B is a top view of the wearable electronic device of FIG. 3A.
Figure 3C:
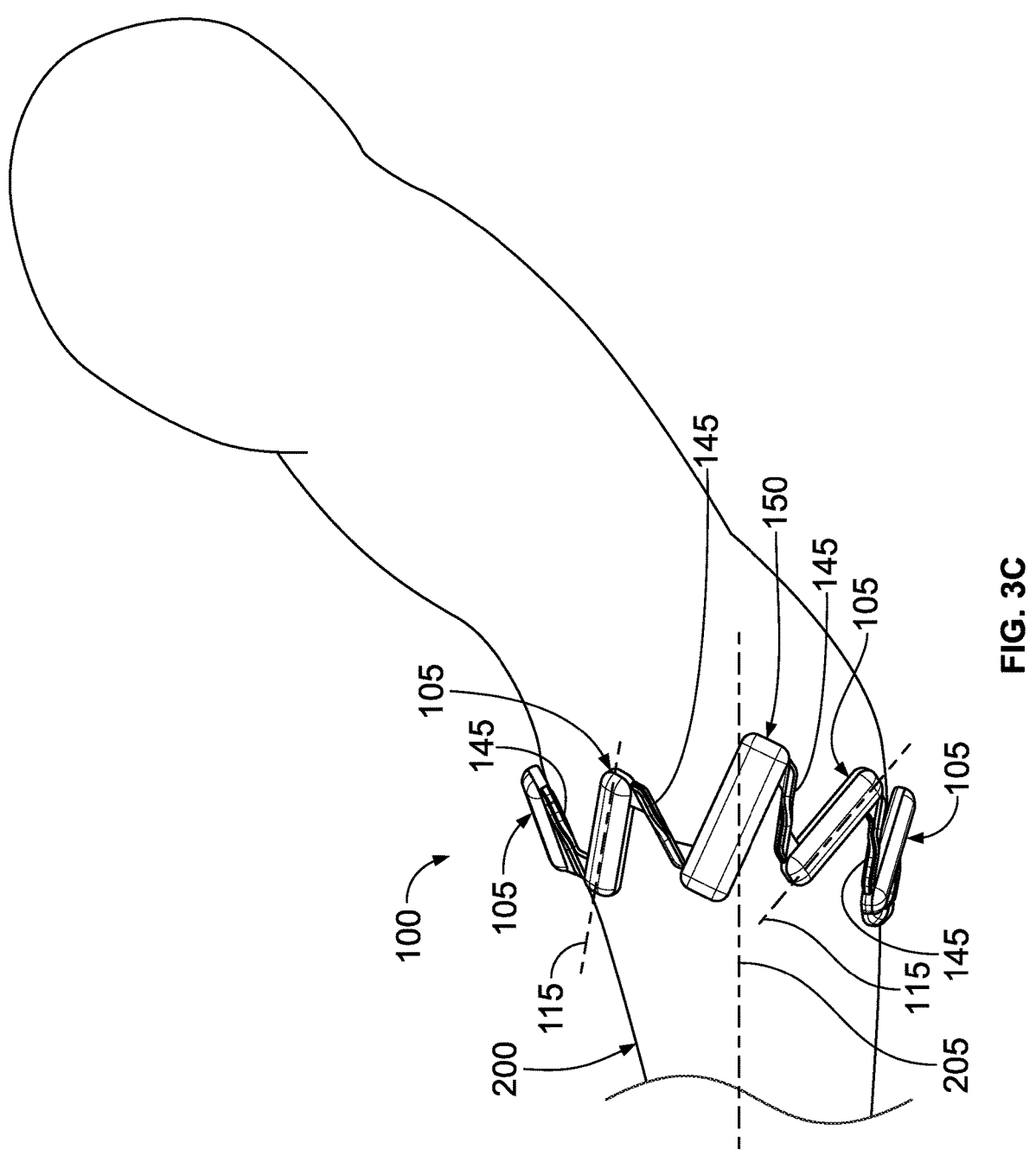
FIG. 3C is a side view of the wearable electronic device of FIG. 3A on a limb (arm) of a user.

Each sensor pod 105 has a longitudinal axis 115 and, as best seen in FIGS. 2C and 3C, with a user wearing wearable electronic device 100 on a limb 200 (shown as a forearm in FIGS. 2C and 3C), the longitudinal axis 115 of adjacent sensor pods 105 are typically generally parallel with a longitudinal axis 205 of the limb 200 with wearable electronic device 100 in a retracted position (FIG. 2C) and can be generally non-parallel with longitudinal axis 205 of the limb 200 with wearable electronic device 100 in the expanded position (FIG. 3C).

Figure 5:
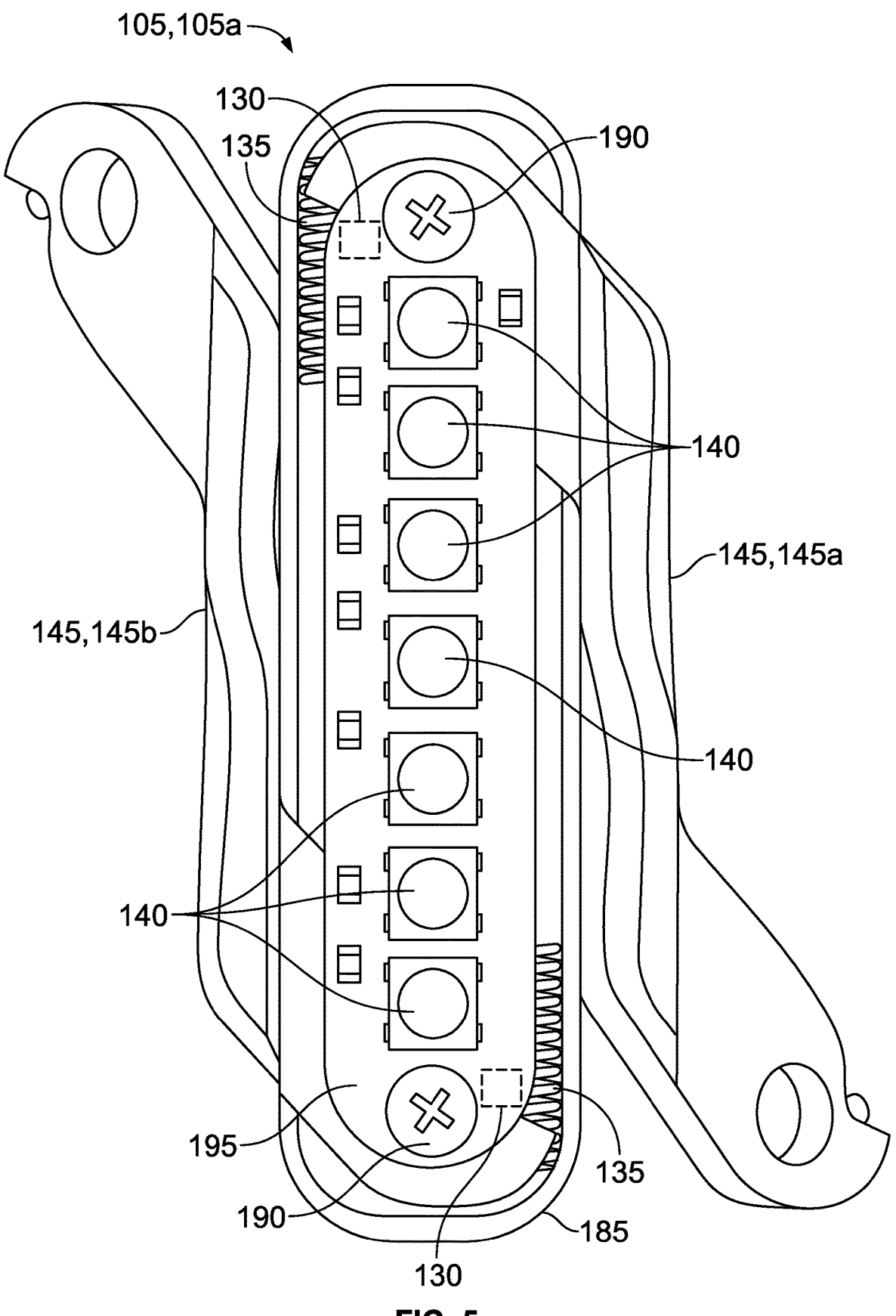
FIG. 5 is a front view of the sensor pod of FIG. 4 with the front housing removed.

As shown in FIG. 5, each sensor pod 105 can also include a plurality of light emitting diodes (LEDs) 140, for example mounted on a printed circuit board 195, which can be configured to illuminate in a predetermined pattern and/or intensity to indicate a strength of a signal detected by biosensors 110 of each sensor pod 105. For example, the predetermined pattern could be a predefined set of one or more colors (e.g., light emitting diodes 140 could illuminate in a blue color to indicate a low strength signal and illuminate in a series of additional colors, such as green, yellow, orange, and red, to indicate increasing strength of signal), a predefined set of one or more illumination intensities (e.g., light emitting diodes 140 could illuminate at a low intensity to indicate a low strength signal and illuminate in greater intensities and the strength of signal increases), and/or a predefined sequence of activating one or more of the LEDs 140 (e.g., the center LED (indicated as 140a) could illuminate to indicate a low strength signal and additional LEDs on opposing sides of center LED 140a could illuminate as the signal strength increases or an end LED (indicated as 140b) could illuminate to indicate a low strength signal and additional LEDs could illuminate in sequence as the signal strength increases). In the example shown, seven LEDs 140 are used, however, any number of LEDs (include one) could be used as desired. Sensor pods 105 have a translucent front housing 180 such that the illumination from LEDs 140 is visible through front housing 180. Alternatively, front housing 180 could be transparent or could be opaque, translucent, or transparent and include apertures through which LEDs protrude.

Figure 9:
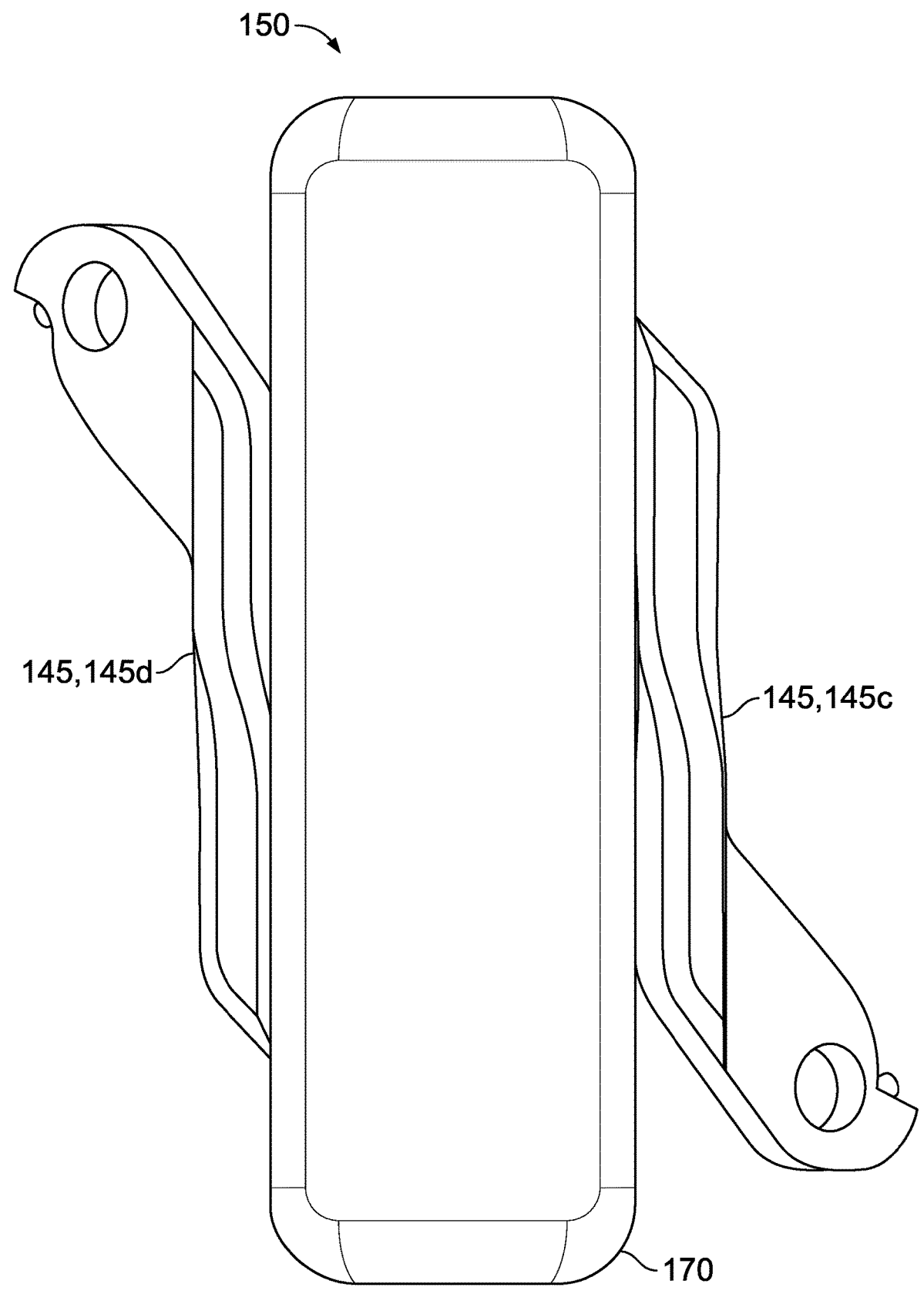
FIG. 9 is a front view of an example main pod of the wearable electronic device of FIG. 1 with two coupling arms.
Figure 10:
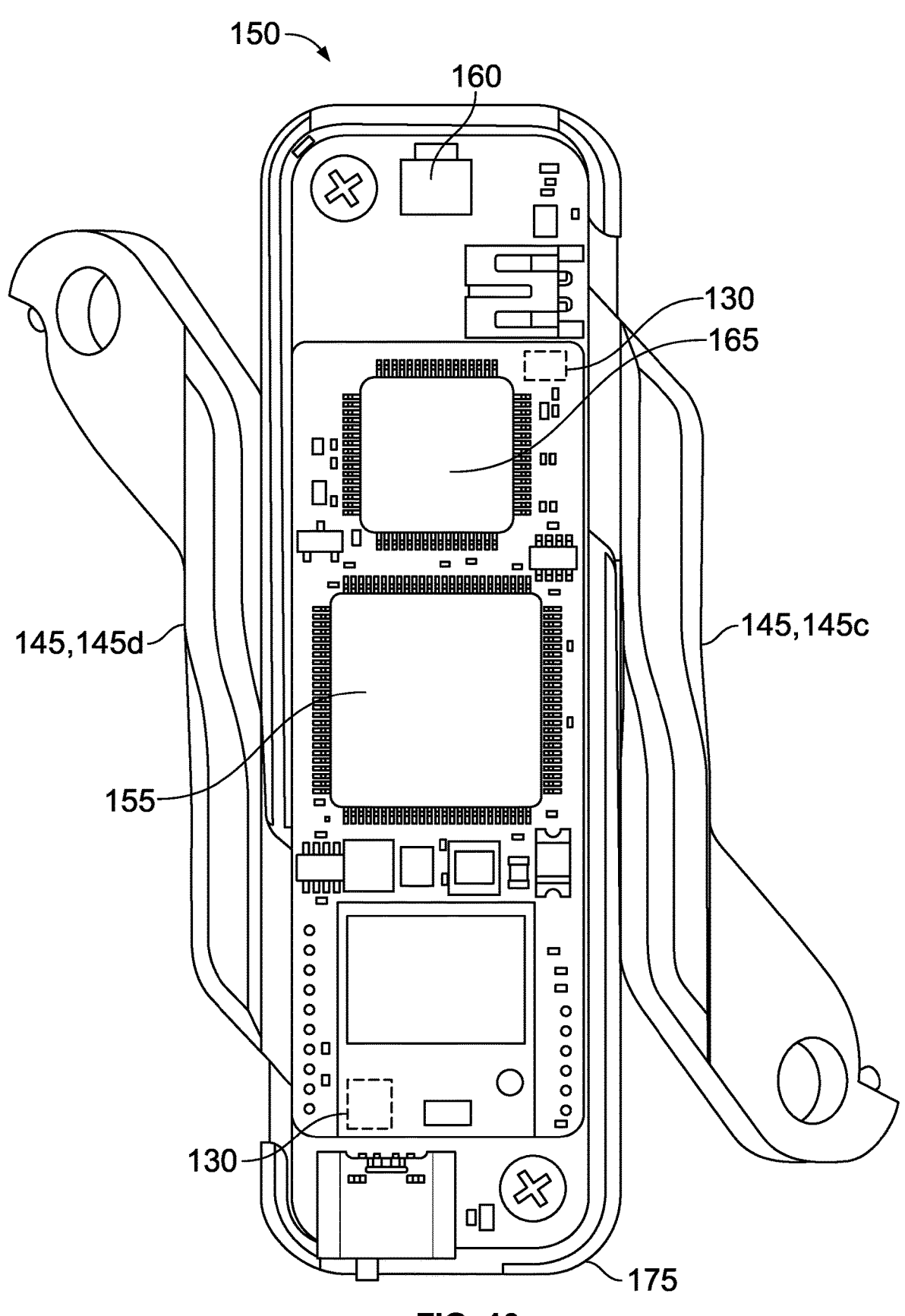
FIG. 10 is a front view of the main pod of FIG. 9 with the front housing removed.
Figure 11:
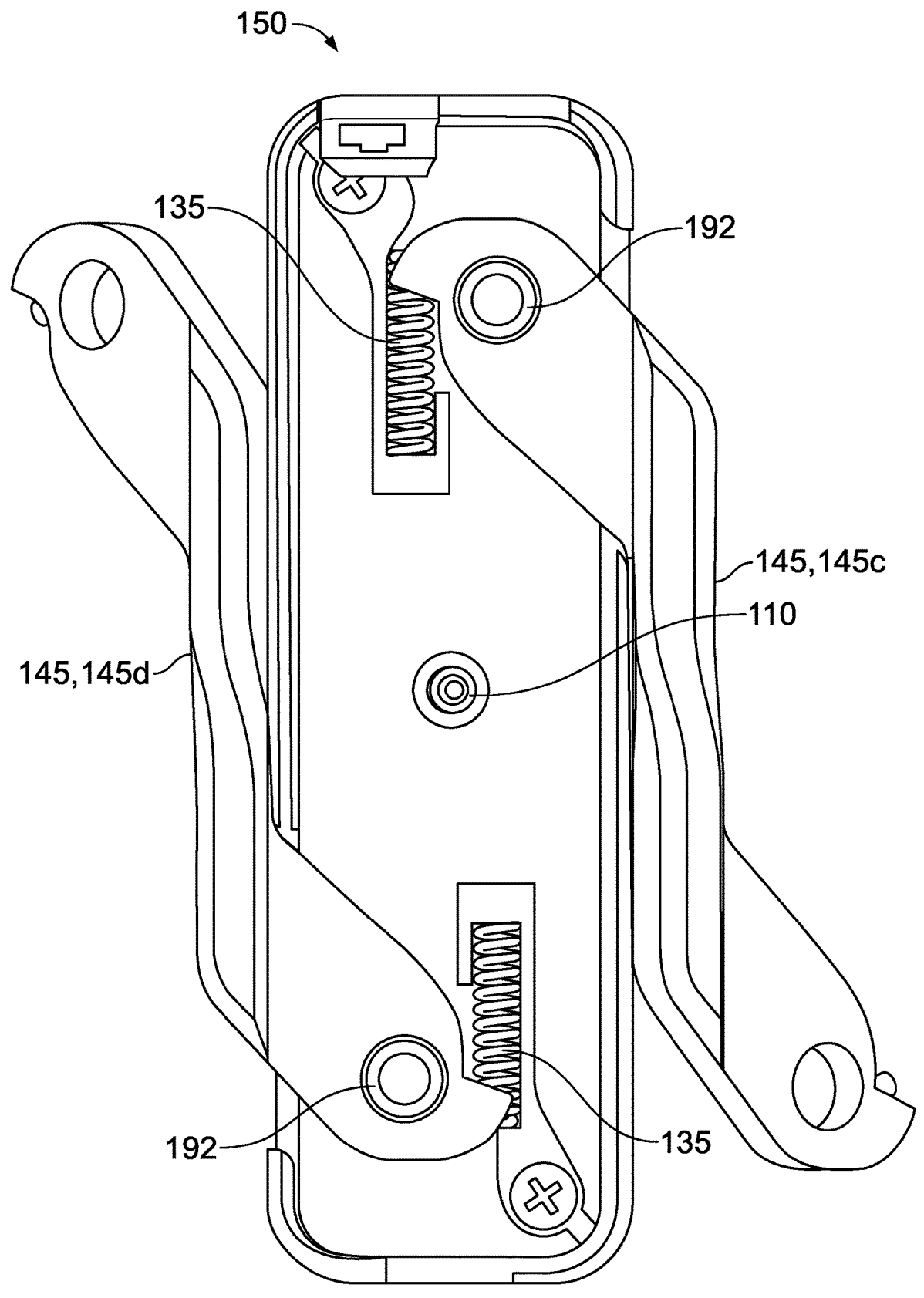
FIG. 11 is a front view of the main pod of FIG. 9 with the front housing and printed circuit board removed.

Referring to FIGS. 9-11, in the example shown, wearable electronic device 100 also includes main pod 150. Although a single main pod is shown in the example, any number of main pods could be used. Main pod 150 could also include one or more biosensors 110, such as those described above in sensor pods 105, that include a portion that extends through a rear housing 175 of main pod 150.

In the example shown, as with sensor pods 105, main pod 150 is rotatably coupled to two coupling arms (indicated as 145c and 145d), positioned on opposite lateral sides of main pod 150. Coupling arm 145c can be rotatably coupled to a first end of main pod 150 at one end of coupling arm 145c and rotatably coupled to an opposite second end of an adjacent sensor pod 105 at an opposite end of coupling arm 145c. Similarly, coupling arm 145d can be rotatably coupled to an opposite second end of main pod 150 at one end of coupling arm 145d and rotatably coupled to an opposite second end of another adjacent sensor pod 105 at an opposite end of coupling arm 145d. In the example shown, coupling arms 145 are rotatably coupled to main pod 150 via protrusions 192 that extends from rear housing 175 through holes in coupling arms 145, but could be rotatably coupled in any appropriate manner desired. Main pod 150 could also include springs 135 (see, e.g., FIG. 11) that are configured to act on a respective coupling arm 145 that is rotatably coupled to main pod 150 to bias coupling arm 145 in a direction to bias main pod 150 and adjacent sensor pods 105 toward the retracted position (see FIGS. 2A-C).

Main pod 150 can also include a position sensor 130 that is configured to measure the rotational position of respective coupling arm(s) 145 relative to main pod 150, as discussed above for sensor pods 105.

Although not shown in the example in FIGS. 9-11, main pod 150 can also include a plurality of light emitting diodes (LEDs) 140, as discussed above for sensor pods 105. Main pod 150 can have a translucent front housing 170 such that the illumination from LEDs 140 is visible through front housing 170. Alternatively, front housing 170 could be transparent or could be opaque, translucent, or transparent and include apertures through which LEDs protrude.

Referring to FIG. 10, in the example shown, main pod 150 of wearable electronic device 100 also includes a processor 155 that is communicatively coupled to biosensors 110 in sensor pods 105 through a wired connection (e.g., running along or through coupling arms 145 and sensor pods 105) or a wireless connection (e.g., via the BLUETOOTH wireless communication standard), to a transceiver 160, and to a memory 165. Memory 165 stores computing instructions, which when executed by processor 155, allows processor 155 to perform various functions, including, by non-limiting example, and of the methods, algorithms, or otherwise functions as described herein. The computing instructions may comprise instructions coded and/or compiled, by way of non-limiting example, via programming languages such as Java, C, C++, C#, python, Go, or the like. Still further, computing device 300 may comprise a memory configured to store computing instructions, for example, as part of an application (app) as downloaded and stored on computing device 300. In various aspects, by way of non-limiting example, computing device 300 may be a computing device such as an APPLE IPHONE mobile device, a GOOGLE ANDROID mobile device, a table, a laptop, or other such existing device upon which apps, computing instructions, or otherwise software may be installed that configures the computing device to communicate, and/or be communicatively coupled (e.g., via data and instruction exchange), to wearable electronic device 100.

For example, in one example aspect, the computing instructions as stored in memory 165 may be accessed and executed by processor 155 could collect biometric signal data of the user from biosensors 110 and transmit the biometric signal data to computing device 300, which could be configured to, via its own computing instructions or app, generate an analysis of the biometric signal data and/or display the biometric signal data and/or an analysis of the biometric signal data on a display screen 305 of computing device 300 (e.g., computing device 300 could display on display screen 305 real-time biosignal intensities from each biosensor 110, could display an indication of the status of the connection for each biosensor 110, can use pattern recognition, machine-learning analysis of the biosignals for virtual limb control and/or game play, etc.). In the alternative, or in addition, processor 155, executing the computing instructions, could receive an input from computing device 300 to configure or alter an operation or setting of wearable electronic device 100 (e.g., processor 155 could receive an input from computing device 300 to turn off or turn on a given sensor pod 105 and/or biosensor 110). In the alternative, or in addition, processor 155 could provide an indication of an operation or status of wearable electronic device 100, for example, via at least one light emitting diode 140 of at least one sensor pod 105 (e.g., processor 155 could illuminate light emitting diodes 140 of a particular sensor pod 105 in a sweeping pattern to indicate a loss of biosignal input from the sensor pod 105, processor 155 could illuminate light emitting diodes 140 in a static pattern to indicate that biosensors 110 of a particular sensor pod 105 have been turned off or not included in any analysis, processor 155 could illuminate light emitting diodes 140 of particular sensor pods 105 in different colors that correspond to a color displayed on display screen 305 of computing device 300 to identify particular sensor pods 105, etc.).

In one example, wearable electronic device 100 could be used with computing device 300, or with a related biometric enabled virtual reality system, to utilize a user's intention to move an extremity to augment a virtual avatar without the need of a visual cue or reference. Wearable electronic device 100 could measure a user's intention to contract a muscle; specifically, through the measurement of biosignals that indicate a physiological intention for a muscle group to contract.

For example, every tissue in the body is electrically active. When a user attempts to initiate a movement, the associated muscles generate electromyographic (EMG) electrical signals with characteristics corresponding to the number of muscle fibers, the intensity of the movement, and duration for which the intended muscles are to contract. By measuring such signals with wearable electronic device 100 and sending these signals to computing device 300, computing device 300, in some aspects, can use machine learning and pattern recognition algorithms to identify the user's intention to activate a specific muscle group-even if the intention is not strong enough, or the user is unable, to provide movement. This aspect becomes increasingly relevant for users that require physical rehabilitation or require kinematic awareness cues to treat an ailment or condition. For example, at least in some aspects, a machine learning model may be trained using a supervised, unsupervised, or reinforcement machine learning program or algorithm. For example, the machine learning program or algorithm may employ a neural network, which may be a deep learning neural network, or a combined learning module or program that learns in two or more features or feature datasets in a particular areas of interest. The machine learning programs or algorithms may also include natural language processing, semantic analysis, automatic reasoning, regression analysis, support vector machine (SVM) analysis, decision tree analysis, random forest analysis, K-Nearest neighbor analysis, naïve Bayes analysis, clustering, reinforcement learning, and/or other machine learning algorithms and/or techniques. Machine learning may involve identifying and recognizing patterns in existing data (such as biometric signal data of one or more user(s)) in order to facilitate making predictions for subsequent data (to predict or otherwise identify the a user's intention to activate a specific muscle group—even if the intention is not strong enough, or the user is unable, to provide movement).

The machine learning model may be created and trained based upon example (e.g., "training data,") inputs or data (which may be termed "features" and "labels") in order to make valid and reliable predictions for new inputs, such as testing level or production level data or inputs.

In supervised machine learning, a machine learning program operating on a server, computing device, or otherwise processor(s), may be provided with example inputs (e.g., "features") and their associated, or observed, outputs (e.g., "labels") in order for the machine learning program or algorithm to determine or discover rules, relationships, or otherwise machine learning "models" that map such inputs to the outputs, for example, by determining and/or assigning weights or other metrics to the model across its various feature categories. Such rules, relationships, or otherwise models may then be provided subsequent inputs in order for the model, executing on a processor (e.g., processor 155), computing device, or otherwise processor(s), to predict, based on the discovered rules, relationships, or model, an expected output, e.g., a user's intention or gesture.

In unsupervised machine learning, the server, computing device, or otherwise processor(s), may be required to find its own structure in unlabeled example inputs, where, for example multiple training iterations are executed by a processor (e.g., processor 155), computing device, or otherwise processor(s) to train multiple generations of models until a satisfactory model, e.g., a model that provides sufficient prediction accuracy when given test level or production level data or inputs, is generated.

Reinforcement learning comprises training a model based on electronic rewards or indications, where the model is trained, over multiple iterations, to take new actions associated with positive results thereby generating a machine learning model configured for a specific use case, e.g., configured for a specific user's biometric signal data, and the specific signals of the user's biometric signal data that indicates a given user intention or gesture of the user (which can, and usually does, differ from user to user).

Supervised learning, unsupervised, and/or reinforcement machine learning may also comprise retraining, relearning, or otherwise updating models with new, or different, information, which may include information received, ingested, generated, or otherwise used over time. The disclosures herein may use one or both of such supervised or unsupervised machine learning techniques.

The number of muscle fibers that are recruited to perform an action as intended by the user are largely influenced by the number of motor neurons innervating said muscle fibers. A number of muscle fibers that are attempting to be recruited to perform a user intention (e.g., flexing a muscle) may be correlated with the perceived effort on behalf of the user to perform said user intention. Furthermore, the location of muscle fibers that are recruited to perform a user intention, based on the specific configuration of wearable electronic device 100, may allow the system to determine which muscle fibers are being recruited to perform a muscle contraction, especially in correspondence to particular muscles and/or muscle groups. The system may use the location of recruited motor neurons, neurons, and/or muscle fibers to determine the intended motion of the user. Subsequent to the identification of the user's intention to activate one or more muscles, and the identification of said muscles, computing device 300 may determine the intended motion on behalf of the user.

In an example, wearable electronic device 100 may receive biometric signal data from the user that corresponds with the brachioradialis muscle and send such signals to computing device 300. In such example, computing device 300 may determine that the user is attempting to perform elbow flexion and modulate a virtual arm displayed on display screen 305 to perform elbow flexion in accordance with the collected biometric signal data, regardless if the user is able to perform elbow flexion in ordinary space. In the same example, if wearable electronic device 100 receives information that many motor neurons are attempting to recruit muscle fibers, the resulting virtual avatar displayed by computing device 300 may represent a more forceful or stronger level of elbow flexion; this aspect becomes especially relevant when determining the amount of intended output strength as initiated by the user. In the same example still, if wearable electronic device 100 receives information relating to fewer motor neurons innervating muscle fibers being recruited, that the user is attempting to perform an isometric contraction—as if to hold an object in virtual space. The above example is intended to be explanatory, and should not be construed as limiting in any fashion.

In the case of a user having an amputation, sometimes the user will experience pain associated with the limb that was amputated—even though there is no physical limb to represent it. This is a phenomenon referred to as Phantom Limb Pain (PLP). Although a portion of a limb of the body may be amputated, in certain users, the nerves that would typically innervate an extremity may still be intact with the muscles in which they are coupled. Thus, a patient's PLP could be treated through "tricking" the brain that the limb is still, in fact, intact. This is done through the user contracting the muscles that correspond to the amputated limb while providing the brain with a kinematic awareness cue of the limb as if it were intact (e.g., a visual representation of the amputated limb). Traditionally, this kinematic awareness cue of the limb is created through recording an uninjured limb with a camera and recreating the image superimposed over the injured limb. The user would simultaneously move the uninjured limb while attempting to contract the injured limb, creating a synchronous muscle contraction, visual cue, and activation of the innervating nerves-causing the brain to interpret the kinematic awareness cue as if the limb were not amputated, and in fact, performing movement the brain would expect through the corresponding muscle contraction. By providing the brain with a kinematic awareness cue of an amputated limb, research has demonstrated statistical significance in reducing the amount of PLP perceived by the user. Wearable electronic device 100 provides for measuring the intention of contracting a particular muscle group without using an uninjured body component as a visual reference via camera, mirror reflection, or similar visual recording technology.

Wearable electronic device 100 and computing device 300 do not require an uninjured limb as a reference to create a kinematic awareness cue to superimpose over the injured limb. Instead, wearable electronic device 100 is used to measure the physiological signals of the limb to detect the intention for a muscle contraction directly. Thus, if a patient has a bilateral amputation, wearable electronic device 100 and computing device 300 can be used on one, or both extremities, to create independent superimposed images of the body components, thus allowing the kinematic awareness cues to be controlled separately. Furthermore, more in-depth analytics such as contraction magnitude, limb orientation, complex movement identification, and gestures can be discerned through the biometric signals that are collected from the patient's injured limb. These biometric signals may then be used by computing device 300 to create a virtual avatar of the injured limb, and through virtual space, project the avatar over where the user's limb would traditionally be; thus, creating a kinematic awareness cue of the injured limb without the need of a reference extremity. The avatar in virtual space may be embodied as a representation of the user's limb, a representation of the biometric signals collected from wearable electronic device 100, an object to be controlled or manipulated, or simply a display of the user's intent to activate a muscle group.

Because the signals generated by wearable electronic device 100 are specific to the user, computing device 300 may use artificial intelligence, including but not limited to deep learning capabilities and/or pattern recognition, to create a biometric user profile that more accurately represents the different states of muscle contraction intention from a user. This allows computing device 300 to improve upon the accuracy and precision of identification of a user's contraction of a muscle, the duration for which the intention to contract a muscle persists, and to the amplitude of which each is occurring.

Additional Considerations

While various embodiments have been described above, this disclosure is not intended to be limited thereto. Variations can be made to the disclosed embodiments that are still within the scope of the appended claims.

The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a processor configured using software, the processor may be configured as respective different hardware modules at different times. Software may accordingly configure a processor, for example, to constitute a particular hardware module at one instance of time and to constitute a different hardware module at a different instance of time.

Hardware modules may provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location, while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other embodiments, the one or more processors or processor-implemented modules may be distributed across a number of geographic locations.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

This detailed description is to be construed as exemplary only and does not describe every possible embodiment, as describing every possible embodiment would be impractical, if not impossible. A person of ordinary skill in the art may implement numerous alternate embodiments, using either current technology or technology developed after the filing date of this application.

Those of ordinary skill in the art will recognize that a wide variety of modifications, alterations, and combinations can be made with respect to the above described embodiments without departing from the scope of the invention, and that such modifications, alterations, and combinations are to be viewed as being within the ambit of the inventive concept.

The patent claims at the end of this patent application are not intended to be construed under 35 U.S.C. § 112(f) unless traditional means-plus-function language is expressly recited, such as "means for" or "step for" language being explicitly recited in the claim(s).

What is claimed is:

1. An annular wearable electronic device, comprising:
a plurality of interconnected sensor pods, each of the plurality of sensor pods including one or more biosensors configured to collect biometric signal data of a user;
wherein
each sensor pod of the plurality of sensor pods is coupled to at least one adjacent sensor pod via a rigid, non-elastic coupling arm such that the rigid, non-elastic coupling arm provides variability in a circumference of the wearable electronic device is variable.

2. The annular wearable electronic device of claim 1, wherein: each of the sensor pods comprises a longitudinal axis; and the longitudinal axes of adjacent sensor pods are generally parallel with a longitudinal axis of a limb of a user wearing the wearable electronic device with the wearable electronic device in a retracted position and generally non-parallel with the longitudinal axis of the limb of the user with the wearable electronic device in an expanded position.

3. The annular wearable device of claim 1, wherein each coupling arm is rotatably coupled to opposite ends of adjacent sensor pods.

4. The annular wearable device of claim 3, wherein each sensor pod comprises a position sensor to measure a rotational position of the coupling arm relative to the sensor pod.

5. The annular wearable device of claim 3, wherein each sensor pod includes a spring configured to act on a respective coupling arm to bias adjacent sensor pods toward a retracted position.

6. The annular wearable device of claim 1, wherein the one or more biosensors comprise: (a) one or more electromyography (EMG) electrodes; (b) one or more electrocardiogram electrodes; (c) one or more photodiodes; (d) one or more ultrasound transducers; (e) one or more accelerometers; (f) one or more gyroscopes; (g) one or more infrared sensors; and/or (h) one or more ultrasound sensors.

7. The annular wearable electronic device of claim 1, comprising:

a processor communicatively coupled to the one or more biosensors;

a transceiver communicatively coupled to the processor; and a memory storing computing instructions, which when executed by the processor, causes the processor to implement at least one of:

(a) collect the biometric signal data of the user and transmit the biometric signal data to a computing device, wherein the computing device is configured to:

(1) generate an analysis of the biometric signal data of the user; and/or (2) display the biometric signal data and/or the analysis thereof on a display screen of the computing device;

(b) receive an input from a computing device to configure or alter an operation or setting of the wearable electronic device; and/or (c) provide an indication of an operation or status of the wearable electronic device via at least one light emitting diode of a sensor pod of the plurality of sensor pods.

8. An annular wearable electronic device, comprising:

a plurality of interconnected sensor pods, each of the plurality of sensor pods including one or more biosensors configured to collect biometric signal data of a user;

wherein each sensor pod of the plurality of sensor pods is coupled to at least one adjacent sensor pod via a rigid, non-elastic coupling arm; and each rigid, non-elastic coupling arm is rotatable relative to each corresponding sensor pod and at least one adjacent sensor pod such that a circumference of the wearable electronic device is variable.

9. The annular wearable electronic device of claim 8, wherein: each of the sensor pods comprises a longitudinal axis; and the longitudinal axes of adjacent sensor pods are generally parallel with a longitudinal axis of a limb of a user wearing the wearable electronic device with the wearable electronic device in a retracted position and generally non-parallel with the longitudinal axis of the limb of the user with the wearable electronic device in an expanded position.

10. The annular wearable device of claim 8, wherein each coupling arm is rotatably coupled to opposite ends of adjacent sensor pods.

11. The annular wearable device of claim 10, wherein each sensor pod comprises a position sensor to measure a rotational position of the coupling arm relative to the sensor pod.

12. The annular wearable device of claim 10, where each sensor pod includes a spring configured to act on a respective coupling arm to bias adjacent sensor pods toward a retracted position.

13. The annular wearable device of claim 8, wherein the one or more biosensors comprise: (a) one or more electromyography (EMG) electrodes; (b) one or more electrocardiogram electrodes; (c) one or more photodiodes; (d) one or more ultrasound transducers; (e) one or more accelerometers; (f) one or more gyroscopes; (g) one or more infrared sensors; and/or (h) one or more ultrasound sensors.

14. The annular wearable electronic device of claim 8, comprising:

a processor communicatively coupled to the one or more biosensors;

a transceiver communicatively coupled to the processor; and a memory storing computing instructions, which when executed by the processor, causes the processor to implement at least one of:

(a) collect the biometric signal data of the user and transmit the biometric signal data to a computing device, wherein the computing device is configured to:

(1) generate an analysis of the biometric signal data of the user; and/or (2) display the biometric signal data and/or the analysis thereof on a display screen of the computing device;

(b) receive an input from a computing device to configure or alter an operation or setting of the wearable electronic device; and/or (c) provide an indication of an operation or status of the wearable electronic device via at least one light emitting diode of a sensor pod of the plurality of sensor pods.

15. An annular wearable electronic device, comprising:

a plurality of interconnected sensor pods, each sensor pod of the plurality of sensor pods including one or more biosensors configured to collect biometric signal data of a user and a plurality of light emitting diodes;

wherein the plurality of light emitting diodes of each sensor pod are configured to illuminate in a predetermined pattern to indicate a strength of a signal detected by the one or more biosensors of the sensor pod.

16. The annular wearable electronic device of claim 15, wherein the predetermined pattern comprises one or more of: a predefined set of one or more colors; a predefined set of one or more illumination intensities; and/or a predefined sequence of activating one or more of the plurality of light emitting diodes.

17. The annular wearable electronic device of claim 15, wherein: each of the sensor pods comprises a longitudinal axis; and the longitudinal axes of adjacent sensor pods are generally parallel with a longitudinal axis of a limb of a user wearing the wearable electronic device with the wearable electronic device in a retracted position and generally non-parallel with the longitudinal axis of the limb of the user with the wearable electronic device in an expanded position.

18. The annular wearable device of claim 15, wherein each coupling arm is rotatably coupled to opposite ends of adjacent sensor pods.

19. The annular wearable device of claim 18, wherein each sensor pod comprises a position sensor to measure a rotational position of the coupling arm relative to the sensor pod.

20. The annular wearable device of claim 18, where each sensor pod includes a spring configured to act on a respective coupling arm to bias adjacent sensor pods toward a retracted position.

21. The annular wearable device of claim 15, wherein the one or more biosensors comprise: (a) one or more electromyography (EMG) electrodes; (b) one or more electrocardiogram electrodes; (c) one or more photodiodes; (d) one or more ultrasound transducers; (e) one or more accelerometers; (f) one or more gyroscopes; (g) one or more infrared sensors; and/or (h) one or more ultrasound sensors.

22. The annular wearable electronic device of claim 15, comprising:

a processor communicatively coupled to the one or more biosensors;

a transceiver communicatively coupled to the processor; and a memory storing computing instructions, which when executed by the processor, causes the processor to implement at least one of:

(a) collect the biometric signal data of the user and transmit the biometric signal data to a computing device, wherein the computing device is configured to:

(1) generate an analysis of the biometric signal data of the user; and/or (2) display the biometric signal data and/or the analysis thereof on a display screen of the computing device;

(b) receive an input from a computing device to configure or alter an operation or setting of the wearable electronic device; and/or (c) provide an indication of an operation or status of the wearable electronic device via at least one of the plurality of light emitting diode of at least one of the plurality of sensor pods.

* * * * *